(12) United States Patent
Schroeder et al.

(10) Patent No.: US 9,796,124 B2
(45) Date of Patent: Oct. 24, 2017

(54) METHOD FOR DETERMINING THE QUALITY OF NON-CROSSLINKED RUBBER MIXTURES, AND CORRESPONDING DEVICE

(75) Inventors: Andreas Schroeder, Weinheim (DE); Lars Wawrzinski, Mannheim (DE); Ludwig Graeff, Viernheim (DE)

(73) Assignee: LANXESS Deutschland GmbH, Cologne (DE)

( * ) Notice: Subject to any disclaimer, the term of this patent is extended or adjusted under 35 U.S.C. 154(b) by 77 days.

(21) Appl. No.: 14/131,562

(22) PCT Filed: Jul. 27, 2012

(86) PCT No.: PCT/EP2012/064787
§ 371 (c)(1),
(2), (4) Date: Sep. 2, 2014

(87) PCT Pub. No.: WO2013/014270
PCT Pub. Date: Jan. 31, 2013

(65) Prior Publication Data
US 2014/0366633 A1  Dec. 18, 2014

(30) Foreign Application Priority Data
Jul. 28, 2011 (EP) .................... 11175837

(51) Int. Cl.
*G01N 29/04* (2006.01)
*B29C 47/92* (2006.01)
(Continued)

(52) U.S. Cl.
CPC ............ *B29C 47/92* (2013.01); *G01N 29/07* (2013.01); *G01N 29/11* (2013.01); *G01N 29/228* (2013.01); *G01N 29/348* (2013.01); *G01N 33/44* (2013.01); *G01N 33/445* (2013.01); *B29C 47/0019* (2013.01); *B29C 2947/924* (2013.01); *B29C 2947/926* (2013.01);
(Continued)

(58) Field of Classification Search
CPC .... B29C 47/92; B29C 47/0019; G01N 29/07; G01N 29/11; G01N 29/228; G01N 29/248; G01N 33/44; G01N 33/445
USPC .................................... 73/598, 600
See application file for complete search history.

(56) References Cited

U.S. PATENT DOCUMENTS 3,779,070 A * 12/1973 Cushman ............. G01N 29/032
                                                73/628
5,062,299 A * 11/1991 Davis ................... G01N 29/032
                                                73/597
(Continued)

FOREIGN PATENT DOCUMENTS

DE       10138790 A1     2/2003

OTHER PUBLICATIONS

Jaunich, Matthias, et al., "Monitoring the vulcanization of elastomers: Comparison of curemeter and ultrasonic online control", Polymer Testing 28 (2009), Elsevier, The Netherlands, pp. 84-88.
(Continued)

*Primary Examiner* — Lisa Caputo
*Assistant Examiner* — Tarun Sinha

(57) ABSTRACT

The invention relates to novel processes for determining the quality of an uncrosslinked rubber mixture by means of ultrasound and to an apparatus suitable for this purpose.

11 Claims, 3 Drawing Sheets

(51) Int. Cl.
*G01N 29/07* (2006.01)
*G01N 29/11* (2006.01)
*G01N 33/44* (2006.01)
*G01N 29/22* (2006.01)
*G01N 29/34* (2006.01)
*B29C 47/00* (2006.01)
*B29K 21/00* (2006.01)
*B29K 105/24* (2006.01)

(52) U.S. Cl.
CPC ............ *B29C 2947/92228* (2013.01); *B29C 2947/92295* (2013.01); *B29C 2947/92704* (2013.01); *B29C 2947/92723* (2013.01); *B29C 2947/92876* (2013.01); *B29K 2021/003* (2013.01); *B29K 2105/246* (2013.01); *G01N 2291/011* (2013.01); *G01N 2291/015* (2013.01); *G01N 2291/0235* (2013.01); *G01N 2291/0289* (2013.01); *G01N 2291/048* (2013.01)

(56) References Cited

U.S. PATENT DOCUMENTS

| | | | | |
|---|---|---|---|---|
| 5,629,485 | A * | 5/1997 | Rose | B64D 15/20 73/170.26 |
| 5,922,598 | A * | 7/1999 | Mintchev | A61K 35/15 424/278.1 |
| 6,134,967 | A * | 10/2000 | White | G01N 29/09 73/588 |
| 8,298,461 | B2 | 10/2012 | Sikora et al. | |
| 8,846,816 | B2 | 9/2014 | Borkowsky et al. | |
| 2004/0006436 | A1 * | 1/2004 | Morgen | G01F 1/668 702/48 |
| 2005/0225734 | A1 * | 10/2005 | De Smit | G03F 7/70341 355/30 |
| 2006/0021642 | A1 * | 2/2006 | Sliwa | B08B 3/02 134/184 |
| 2006/0266119 | A1 * | 11/2006 | Cobb | G01N 29/07 73/579 |
| 2010/0136696 | A1 * | 6/2010 | Schaefer | G01N 22/00 436/20 |
| 2011/0183422 | A1 | 7/2011 | Cronvall et al. | |
| 2013/0001466 | A1 | 1/2013 | Schroeder et al. | |

OTHER PUBLICATIONS

European Search Report from European Application No. 11175837, dated Nov. 29, 2011, two pages.

Schroeder et al., "Very Fine Dispersable Polymer Bound Additives", Kautschuk Gummi Kunststoffe, 11, 2008, Gelnhausen, Germany pp. 584 to 596.

Payne, A.R., et al. "Carbon Black Structure in Rubber" Rubber Chem. and Technol. 36 (1963) No. 1, ACS, Cleveland, Ohio, pp. 147-155.

Schnetger, Lexikon Kautschuktechnik [Encyclopedia of rubber technology], Heidelberg, Germany, 3rd revised addition (2004), pp. 557-558.

Kirchhoff, J.et al., "Measuring the State of Cure of Elastomers by using an Ultrasonic Technique", KGK Kautschuk Gummi Kunststoffe, 55 Jahrgang, Nr. Jul. 8, 2002, Geinhausen, Germany, pp. 373-381.

* cited by examiner

METHOD FOR DETERMINING THE QUALITY OF NON-CROSSLINKED RUBBER MIXTURES, AND CORRESPONDING DEVICE

The invention relates to novel processes for determining the quality of an uncrosslinked rubber mixture by means of ultrasound and to an apparatus suitable for this purpose. The process of the invention permits not only the detection of particulate contaminants but also determination of the quality of dispersion of solids in the uncrosslinked rubber mixture. Both criteria are quality-determining for rubber mixtures.

BACKGROUND INFORMATION

Ultrasound analysis has only very restricted use for uncrosslinked rubber mixtures comprising fillers or comprising other substances, because of the high level of attenuation of the sound. A simple and rapid method is required for the determination of particulate contaminants and the degree of dispersion thereof in an uncrosslinked rubber mixture.

Rubber is used for various technical components, such as tires, engine bearings, O-rings, etc. Even individual coarse-particle contaminants≥100 μm lead to early failure of the rubber components, in particular under dynamic load [A. Schrdder et al., Kautschuk, Gummi Kunststoffe, 11, pp. 584 to 596, 2008]. In the case of very thin-walled components (1 mm), such as O-rings, this type of particulate contamination can impair sealing properties. In the case of profiles, the appearance of the components requires that particulate contaminants be avoided.

The degree of dispersion of the substances within the rubber, in contrast, also determines the dynamic-mechanical property profile of the crosslinked rubber mixture and thus determines the quality of the technical components composed thereof. By way of example, hysteresis increases, and with this the rolling resistance of a tire increases, if the reinforcing nanoscale fillers are inadequately deagglomerated and dispersed [Payne, A. R.; Watson, W. F.: Rubber Chem. and Technol. 36 (1963) No. 1, pp. 147-155].

Until now, the quality of an uncrosslinked rubber mixture has been monitored only by taking individual samples (<0.1% of the total quantity). The Mooney viscosity of the rubber and the crosslinking curves of the individual samples are determined. The tensile properties of the mixture are determined after vulcanization of individual samples [J. Schnetger, Lexikon Kautschuktechnik [Encyclopedia of rubber technology], Heidelberg, 3rd revised edition (2004), 388-391]. These tests do not reveal small numbers of individual coarse-particle contaminants. On the basis of the test results it is moreover impossible to decide whether any deviation from the specifications involves particulate contaminants or other defects. Individual samples are also subjected to optical microscopy [J. Schnetger, Lexikon Kautschuktechnik [Encyclopedia of rubber technology], Heidelberg, 3rd revised addition (2004), 448-449]. Although this can reveal individual contaminants, full quality control of the rubber mixture is not achieved. Furthermore, it is advantageous to vulcanize the sample. The individual samples are not representative, because of their small number. The assessment of the samples by what is known as the Cabot method for deagglomeration of carbon black materials is moreover subjective. The quality controls described are moreover carried out manually, and not before some minutes or indeed days have expired since production of the rubber mixture. The method is time-consuming, since the test is carried out manually and off-line.

Ultrasound is used for the determination of coarse defects in materials which are good ultrasound conductors, for example metals or liquids. Measurements here are made in reflection by the pulse-echo method. The ultrasound frequency spectrum can also be used to determine the particle size distribution in low-viscosity suspensions, for example aqueous suspensions or polymer melts [U.S. Pat. No. 5,121, 629]. The rubber industry also uses ultrasound for the quality control of crosslinked components [J. Schnetger. Lexikon Kautschuktechnik [Encyclopedia of rubber technology], Heidelberg, 3rd revised addition (2004), 557-558].

In contrast, unvulcanized rubber mixtures are very poor conductors of ultrasound, because of their viscoelastic properties, and because the content of nanoscale fillers is often very high [J. Schnetger, Lexikon Kautschuktechnik [Encyclopedia of rubber technology], Heidelberg, 3rd revised addition (2004), 557-558]. The ultrasound therefore penetrates only to a small depth into an uncrosslinked rubber mixture. It is therefore possible to test thin-walled unvulcanized rubber samples which the sound is just capable of penetrating. In J. Kirchhoff, et al., Gummi Kunststoffe, 55 (2002) 373-381, the crosslinking behavior of rubber mixtures is carried out by taking individual samples measuring 2 mm. In EP-2314442 A, the quality of a rubber mixture in respect of the dispersion of crosslinking chemicals is determined by means of a marker with particle size<100 μm and with density>2 g/cm$^3$. The thickness of the sample here is only 4 mm.

There is therefore no process known within the prior art that permits very simple, unambiguous, rapid and effective quality control of uncrosslinked rubber mixtures.

It was therefore an object of the present invention to provide a novel and easily operatable process for the rapid and dependable control of the quality of uncrosslinked rubber mixtures, i.e. a process suitable for the detection of particulate contaminants with diameter>10 μm, and also an apparatus suitable for said use.

SUMMARY OF THE INVENTION

Surprisingly, the object underlying this invention was achieved in that, during extrusion, uncrosslinked rubber mixtures are analyzed via simultaneous measurement of ultrasound transmission at relatively high temperatures within a suitable frequency range with reference to alternations caused by particulate contaminants, and also changes in the degree of dispersion of solids therein, without any requirement for the presence of markers or the like.

DESCRIPTION OF THE EMBODIMENTS

Figure 1:
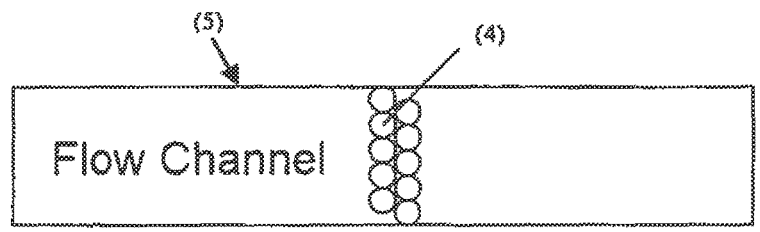
FIG. 1 shows a plan view of detection segment with sensors for ultrasonic detection of contaminants in a flow of uncrosslinked rubber.

The present invention therefore provides a novel process for the determination of the quality of an uncrosslinked rubber mixture, i.e. a process for the detection of particulate contaminants with diameter>10 µm in an uncrosslinked rubber mixture via measurement of the transmission of ultrasound at temperatures above 25° C., preferably above 80° C., particularly preferably above 100° C. and frequencies of from 0.5 MHz to 20 MHz, where the ultrasound signal is preferably transmitted over a distance≥10 mm.

The frequency of the ultrasound signal here is preferably from 0.5 MHz to 20 MHz, particularly preferably from 2 MHz to 10 MHz, very particularly preferably from 4 MHz to 7 MHz. A large portion of the rubber mixture is analyzed by the ultrasound here: ≥1%, preferably ≥10%, particularly preferably 100%, of the rubber mixture. This method therefore permits representative quality control of uncrosslinked rubber mixtures, rather than merely testing of individual samples.

This method is successful in detecting meaningful signals relating to particulate contaminants, and also changes in the degree of dispersion of solids and deagglomeration in a rubber mixture, and is thus successful in controlling the quality of the uncrosslinked rubber mixture.

Particularly suitable rubbers are natural rubber (NR), isoprene rubber (IR), styrene-butadiene rubber (SBR), butadiene rubber (BR), isoprene-isobutylene rubber (IIR), polychloroprene rubber (CR), acrylonitrile-butadiene rubber (NBR), hydrogenated acrylonitrile-butadiene rubber (HNBR), carboxylated acrylonitrile-butadiene rubber (XNBR), hydrogenated carboxylated acrylonitrile-butadiene rubber (HXNBR), ethylene-propylene-diene rubber (EPDM), ethylene-propylene rubber (EPM), fluoro rubber (FKM), perfluorinated fluoro rubber (FFKM), acrylate-ethylene rubber (AEM), acrylate rubber (ACM), ethylene-ethylene-methylene-acrylate rubber (EMA), chlorinated polyethylene, chlorosulfonated polyethylene, ethylene-vinyl acetate rubber (EVA), silicone rubber, fluorosilicone rubber, ethylene-epichlorohydrin rubber (ECO), epichlorohydrin rubber (CO) and/or polyurethane rubber (PU).

The rubber mixture preferably involves mixtures of rubbers with fillers, crosslinking agents, antioxidants, plasticizers and/or other auxiliaries.

Examples of fillers for the purposes of the invention are pale-colored inorganic fillers, e.g. mica, kaolin, siliceous earth, silica, chalk, talc powder, carbon fillers, e.g. carbon black, graphite, carbon nanotubes, magnetizable fillers, such as carbonyl iron powder, iron oxides, ferrites and/or fibers, e.g. aramid fiber pulp, carbon fibers.

For the purposes of the invention, crosslinking agents are: materials forming network nodes, e.g.
- sulfur (soluble or insoluble) and/or sulfur donors, e.g. dithiomorpholines (DTDM), tetramethylthiuram disulfides (TMTD), tetraethylthiuram disulfide (TETD), dipentamethylenethiuram terasulfides (DPTT), phosphoryl polysulfides, e.g. Rhenocure® SDT/S from Rhein Chemie Rheinau GmbH and/or
- peroxides, e.g. di-tert-butyl peroxide, di-(tert,butyl-peroxy-timethyl-cyclohexanes, di-(tert-butylperoxyisopropyl)benzenes, dicumyl peroxides, dimethyldi(tert-butylperoxy)hexynes, butyl-di-(tert-butylperoxy) valerates,
- resorcinol, aldehyde-amine condensates, e.g. hexamethylenetetramines, resorcinol-formaldehyde precondensates and/or vulcanization resins, for example halomethylphenolic resin,
- quinone dioximes
- bisphenols, accelerators, e.g.
- carbamates and triazines, e.g. hexamethylenediamine carbamate (HMDC), organic triazines,
- thiazoles, e.g. 2-mercaptobenzothiazole (MBT), zinc mercaptobenzothiazole (ZnMBT), thiadiazoles (TDD),
- sulfenamides, such as cyclohexylbenzothiazolesulfenamides (CBS),
- dibenzothiazyl disulfide (MBTS), butylbenzothiazolesulfenamides (TBBS), dicyclohexylbenzothiazolesulfenamide (DCBS), 2-(4-morpholinylmercapto)benzothiazole (MBS),
- thiurams, such as tetramethylthiuram monosulfide (TMTM), tetraethylthiuram disulfide (TETD), tetramethylthiuram disulfide (TMTD), tetrabenzylthiuram disulfide (TBTD), dipentamethylenethiuram tetra(hexa)sulfide (DPTT),
- dithiocarbamates, such as Zn dimethyldithiocarbamates (ZDMC), Cu dimethyldithiocarbamates, Bi dimethyldithiocarbamates, Zn diethyldithiocarbamates (ZDEC), tellurium diethyldithiocarbamates (TDEC), Zn dibutyldithiocarbamates (ZDBC), Zn ethylphenyldithiocarbamates (ZEPC), Zn dibenzyldithiocarbamates (ZBEC), Ni dibutyldithiocarbamates (NBC), selenium diethyldithiocarbamates (SeEDC), selenium dimethyldithiocarbamates (SeDMC), tellurium diethyldithiocarbamates (TeEDC),
- thiophosphate and dithiophosphate, e.g. zinc O,O-di-n-butyl dithiophosphate (ZBDP), zinc O-butyl O-hexyl dithiophosphate, zinc O,O-diisooctyl dithiophosphate (ZOPD), dodecylammonium diisooctyl dithiophosphate (AOPD), e.g. Rhenogran® products ZDT, ZAT, ZBOP from Rhein Chemie Rheinau GmbH,
- ureas/thioureas, e.g. ethylenethiourea (ETU), N,N,N'N'-tetramethylthiourea (TMTU), diethylthiourea (DETU), dibutylthiourea (DBTU), 3-(3,4-dichlorophenyl)-1,1-dimethylurea (diuron) etc., and/or
- xanthogenate accelerators, e.g. zinc isopropyl xanthogenate (ZIX),
- guanidines, e.g. diphenylguanidine (DPG) and/or N',N-di-ortho-tolylguanidine (DOTG) and the guanidine-free replacement accelerators, such as Rhenogran® XLA 60, retarders, e.g.
- N-nitrososdiphenylamine, N-cyclohexylthiophthalimide (CPT), e.g. Vulkalent® G, sulfonamide derivatives (e.g. Vulkalent® E/C), phthalic anhydride (Vulkalent® B/C), where both of the Vulkalent® products are obtainable from Lanxess Deutschland GmbH, and also Benzoic anhydride.

Examples of antioxidants for the purposes of the invention are colorant and non-colorant antioxidants, e.g. paraphenylenediamines, isopropylphenylparaphenylenediamine (IPPD), paraphenylenediamine (6PPD), N,N-ditolyl-p-phenylenediamines (DTPD), etc., amines, e.g. trimethyl-1,2-dihydroquinoline (TMQ), (phenyl)[amines]-1,4-naphthalenedione (PAN), bis(4-octylphenyl)amine (ODPA), styrenized diphenylamine (SDPA), mono- and bisphenols, e.g. 2,2'-methylenebis(4-methyl-6-tert-butylphenol) (BPH), 2,2'-isobutylidenebis(4,6-dimethylphenol) (NKF), 2,2'-dicyclopentadienylbis(4-methyl-6-tert-butylphenol) (SKF), 2,2'-methylenebis(4-methyl-6-cyclohexylphenol) (ZKF), 2,6-ditert-butyl-p-cresol (BHT), substituted phenol (DS), styrenized phenols (SPH), mercaptobenzimidazoles, e.g. 2-mercaptobenzimidazole (MBI), 2-mercaptomethylbenzimidazoles (MMBI), zinc 4- and 5-methyl-2-mercaptobenzimidazoles (ZMMBI), etc., olefins, paraffinic and/or aromatic plasticizers. The composition here is adapted to be appropriate to the desired final product.

Examples of plasticizers for the purposes of the invention are long-chain esters and/or ethers, for example thioesters, phthalic esters, alkylsulfonic esters, adipic esters, sebacic esters, dibenzyl ethers, and/or mineral oils (paraffinic, aromatic naphthenic or synthetic oils).

Examples of auxiliaries for the purposes of the invention are dispersing agents, e.g. fatty acids, stearic acid and/or oleic acid and/or activators, for example zinc oxide, lead oxide, bismuth oxide, lithium carbonate, sodium carbonate and/or calcium hydroxide, magnesium oxide, flame retardants, such as antimony oxide, coupling agents, such silanes, etc.

All of the abovementioned products are commercially available products which are optionally also used in granulated form for example as polymer-bound additives and/or as the crosslinking agent masterbatches described in EP2314442A.

The uncrosslinked rubber mixtures involve masterbatches, parent mixtures and crosslinkable rubber mixtures.

Masterbatches preferably comprise:
from 2.5 to 90% by weight of rubber
from 0 to 50% by weight of plasticizers
from 0 to 97.5% by weight of fillers
from 0 to 80% by weight of crosslinking agents
from 0 to 20% by weight of dispersing agents
from 0 to 80% by weight of activators and
from 0 to 50% by weight of antioxidants.

Parent mixtures preferably comprise
100 phr of rubber
from 0 to 100 phr of plasticizers
from 0 to 500 phr of fillers
from 0 to 30 phr of auxiliaries and
from 0 to 10 phr of antioxidants.

Crosslinkable rubber mixtures are parent mixtures which also comprise from 0 to 20 phr of crosslinking agents.

Preference is given to crosslinkable rubber mixtures.

Particular preference is given to crosslinkable rubber mixtures which comprise inter alia from 30 to 90 phr of carbon black and/or silica, from 3 to 7 phr of zinc oxide, and also from 0.5 phr to 4 phr of sulfur and from 1 to 5 phr of accelerator.

The masterbatches, the parent mixture and the crosslinkable rubber mixture are preferably produced by the methods familiar to the person skilled in the art, for example those described in PCT/EP2009/058041. Fillers, auxiliaries, crosslinking agents and/or antioxidants are mixed here together with the rubber in a mixing assembly. Examples of suitable mixing assemblies are internal mixers, roll mills, extruders.

In another embodiment of the invention, the parent mixture is produced in a mixing assembly in a first step. Temperatures above 130° C. can be reached here. In a second production step, crosslinking agents are added to the parent mixture in another mixing assembly, after cooling of the parent mixture to temperatures below 130° C. The crosslinking agents here can to some extent already be added to the parent mixture in the first production step.

Particular preference is given here to continuous processes in which the masterbatches, parent mixtures, or else the crosslinkable rubber mixtures are produced in an extruder.

Very particular preference is given to the production process described in DE-A-102008040138 for crosslinkable rubber mixtures which produces the parent mixture in a batch process in a kneader and adds, to the parent mixture, crosslinking agents in the form of the crosslinking agent masterbatches described in EP-A-2314442, and mixes the crosslinking agent masterbatches with the parent mixture in a continuous process using an extruder.

The contaminants are present in the raw materials used, such as rubber, fillers, antioxidant, crosslinking agent and/or auxiliaries, and/or are produced during the mixing process and/or are added unintentionally.

Examples of contaminants present in the raw materials used are inadequately dispersed agglomerates of fillers, solid particles made of crosslinking agent, of auxiliary and of antioxidants preferably with a high melting point above 100° C., grit, for example from the production of carbon blacks, and contaminants in the rubber, particularly in the natural rubber, for example small stones, wood splinters, etc.

Examples of contaminants produced during the process of mixing of the uncrosslinked rubber mixture are incipiently crosslinked residues of rubber mixtures in mixing assemblies, and abraded metal from the mixing assemblies.

Examples of contaminants added unintentionally are wood splinters from pallets, mechanically derived plastics, particles, small screws, etc.

The diameter of the particulate contaminants here is preferably >10 μm, preferably >100 μm and very particularly preferably >500 μm. The particulate contaminants here are solids with melting point>80° C., preferably >100° C., particularly preferably >120° C., very particularly preferably >150° C.

Differences in the degree of dispersion of fillers in the uncrosslinked rubber mixture result in poor mixing of the solids and/or deagglomeration thereof.

In one embodiment of the process of the invention, at least one pair, preferably at least one detection band of at least two pairs, of ultrasound sensors is used to detect the particulate contaminants and differences in the degree of dispersion in uncrosslinked rubber mixtures. The respective sensors of a pair are opposite, and the arrangement has the pairs in a row alongside one another. The distance between the sensors of a pair is preferably >10 mm. One ultrasound sensor of a pair here functions as transmitter, and the other sensor functions as receiver of the ultrasound signal. The uncrosslinked rubber mixture is present in the gap between the sensors. There is preferably direct contact here between sensors and uncrosslinked rubber mixture. The gap is preferably delimited at the sides, thus giving a flow channel preferably with height≥10 mm, particularly preferably with height≥20 mm, very particularly preferably with height 30 mm. The width of the flow channel is preferably ≥20 mm, particularly preferably ≥50 mm, very particularly preferably ≥100 mm. The velocity of the uncrosslinked rubber mixture as it passes through the detection band is preferably 0.1 m/min., particularly preferably 1 in/min., very particularly preferably 10 m/min. An extruder is preferably used here. At the same time, the intensity of the transmitted ultrasound signal is measured at the receiver during the processing time. For the purposes of the invention, the processing time is the extrusion time. The ultrasound signal is recorded and evaluated with the aid of an electronic ultrasound testing system and of an evaluation unit, for example an oscilloscope or preferably a computer. When coarse-particle contamination passes through the system, the intensity of the ultrasound signal at the receiver is reduced by scattering and/or reflection of the sound waves at said coarse-particle contamination.

In one preferred embodiment of the process of the invention, the ultrasound signal is emitted in the form of needle pulses or series of needle pulses, known as bursts. The time elapsed between the individual needle pulses or bursts is preferably at least ≤1 s, particularly preferably at least ≤100 ms. Another variable measured in addition to the transmission of the intensity, is the time required by the signal to travel from the transmitter to the receiver. The velocity of the sound is determined from the known path length. The velocity of the sound is only slightly altered when coarse-particle contaminants pass through the system. When relatively small particles, for example highly deagglomerated filler entities<1 μm, pass through the system, the velocity of the sound is also altered. It is thus possible to distinguish between coarse-particle contaminants and other contaminants.

Individual contaminants in the uncrosslinked rubber lead to reduced signal intensity (peak) at the receiver. In another preferred embodiment of the process of the invention, the size of the coarse-particle contaminants is determined from the duration of the reduction of signal intensity and from the flow velocity. By using the evaluation unit it is possible to determine a particle size distribution from the number of peaks and their width. Defective regions of the rubber mixture can be removed after discharge from the flow channel.

In another preferred embodiment of the process of the invention, the extruder is simultaneously used as mixing assembly for the rubber mixture.

In one preferred embodiment of the process of the invention, the rubber passes through a detection band composed of at least one ultrasound sensor pair arranged across the entire width of the flow channel.

In one very particularly preferred embodiment of the invention, the rubber mixture passes through two slightly offset detection bands. This ensures that the entire rubber mixture is analyzed.

The invention also provides an apparatus for carrying out the process of the invention, comprising an arrangement of an extruder (1), of at least one detection band made of at least one ultrasound sensor pair (4) and of the flow channel (5), and of an evaluation unit (3).

The apparatus of the invention is preferably described in the figures below, but is not restricted thereto.

Figure 2:
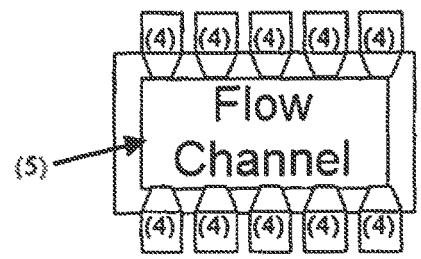
FIG. 2 provides a side view of the sensor arrangement of FIG. 1.
Figure 3:
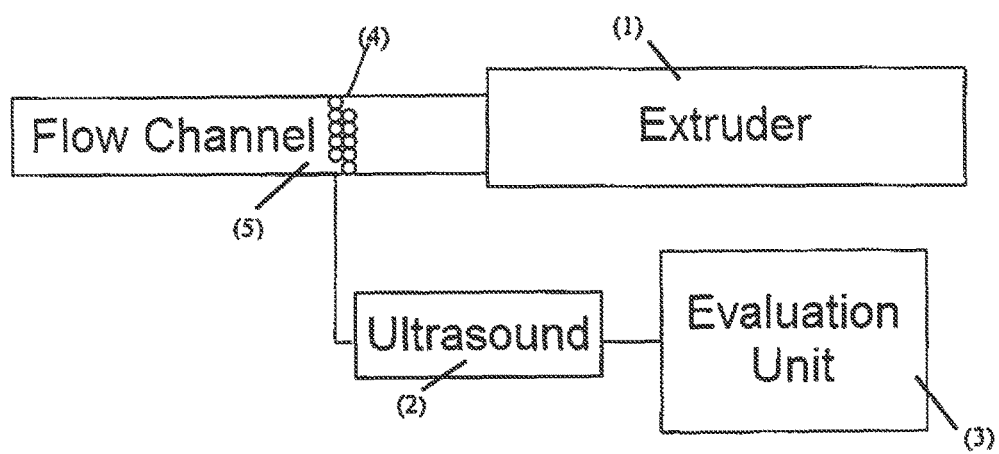
FIG. 3 shows an embodiment of a detection arrangement for analyzing contaminants in a flow of uncrosslinked rubber.

FIG. 1 shows by way of example a plan view of the detection band, composed of the ultrasound sensor pairs (4), i.e. one transmitter and one receiver in each pair, and of the flow channel (5), and FIG. 2 depicts a side view of the arrangement in FIG. 1. FIG. 3 shows an arrangement of an extruder (1), of the detection band, composed of the ultrasound sensor pairs (4) and of the flow channel (5) and of the electronic ultrasound testing system (2), and of a computer as evaluation unit (3).

The invention also provides the use of the apparatus of the invention for determination of quality in an uncrosslinked rubber mixture and for the production of uncrosslinked rubber mixtures.

The invention also concomitantly provides the use of the uncrosslinked rubber mixture produced by the process of the invention, for tires, profiles, O-rings and components for vibration control.

The examples and figures below serve for explanation of the invention, without any resultant limiting effect.

INVENTIVE EXAMPLES

Example 1

A parent mixture composed of 100 phr of SMR10 natural rubber, 50 phr of N550 carbon black, 5 phr of Naftolen ZD plasticizer, 5 phr of ZnO, 1 phr of stearic acid was produced using an internal mixer. About 1 kg of said mixture was extruded through a flow channel by an EEK32.12L single-screw extruder from Rubicon. The length of the flow channel is 300 mm, its height is 20 mm and its width is 15 mm. In the middle of the flow channel there is a detection band composed of a pair of K4V1 ultrasound sensors from GE Sensing & Inspection Technologies GmbH with an average frequency of 4 MHz. The diameter of the oscillator of the ultrasound sensor here is 7 mm. Every 100 ms, the one of the sensors emits a needle pulse, which is received by the other sensor. The sensors were controlled by way of the USLT 2000 electronic testing system from GE Sensing & Inspection Technologies GmbH, and the test signals received were passed by way of the electronic testing system to a computer, where they were processed. The temperature of the extruder, and also the flow channel, was controlled to 100° C. The rotation rate of the extruder was 20 rpm. Throughput was about 100 g/min. This gave an extrusion rate of about 0.25 m/min. The average residence time from the feed to the detection band was about 2 min.

Figure 4:
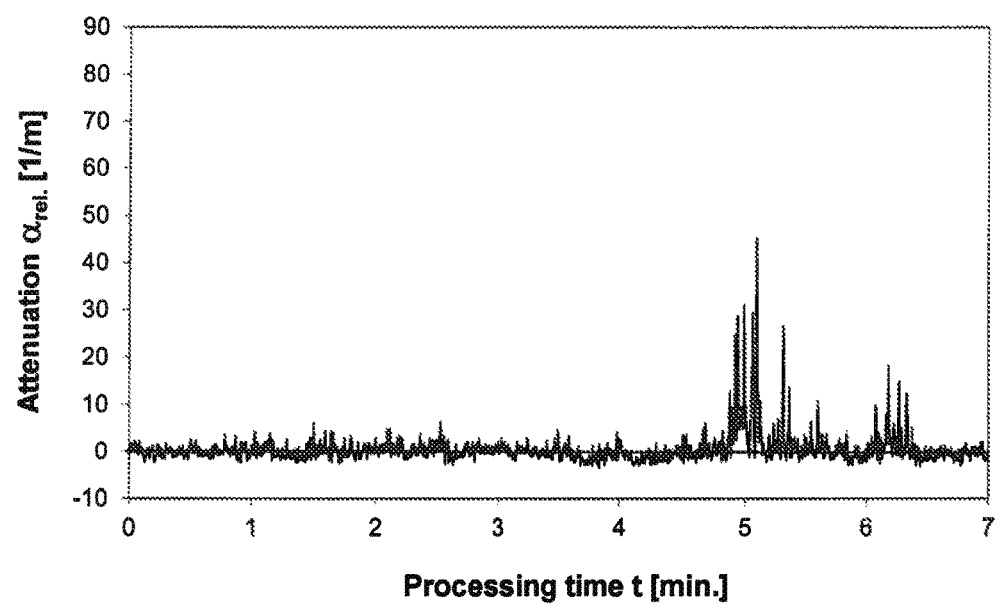
FIG. 4 provides an example of test data showing the relative attenuation coefficient for the processing time during analysis of an uncrosslinked rubber mixture.

FIG. 4 shows the test data.

FIG. 4 plots the relative attenuation coefficient $\alpha_{rel.}$ against the processing time t of the mixture. The rel. attenuation coefficient $\alpha_{rel.}$ is the standardized n.egative natural logarithm of the quotient calculated by dividing the transmitted intensity I(t) of the ultrasound signal at the time t by the average transmitted intensity in the time range from t=0 to t=5 min., i.e. by the average transmitted intensity $I_{average}$ of the parent rubber mixture without contaminants. The path length s of the ultrasound corresponds to the thickness of the sample.

$$\alpha_{rel.}(t) = -\ln(I(t)/I_{average})/s$$

At the time t=3 min., about 0.5 g of mechanically derived plastics particles with particle size about 2 mm to 5 mm are added irregularly for about 2 min. After about 2 min. of residence time in the extruder, large variations were observed in the attenuation coefficient (FIG. 4). Attenuation increased greatly because of the scattering of the ultrasound signal at the coarse plastics particles. Contaminants, for example in this case the mechanically derived plastics particles, can be detected unambiguously by the process of the invention.

Example 2

Figure 6:
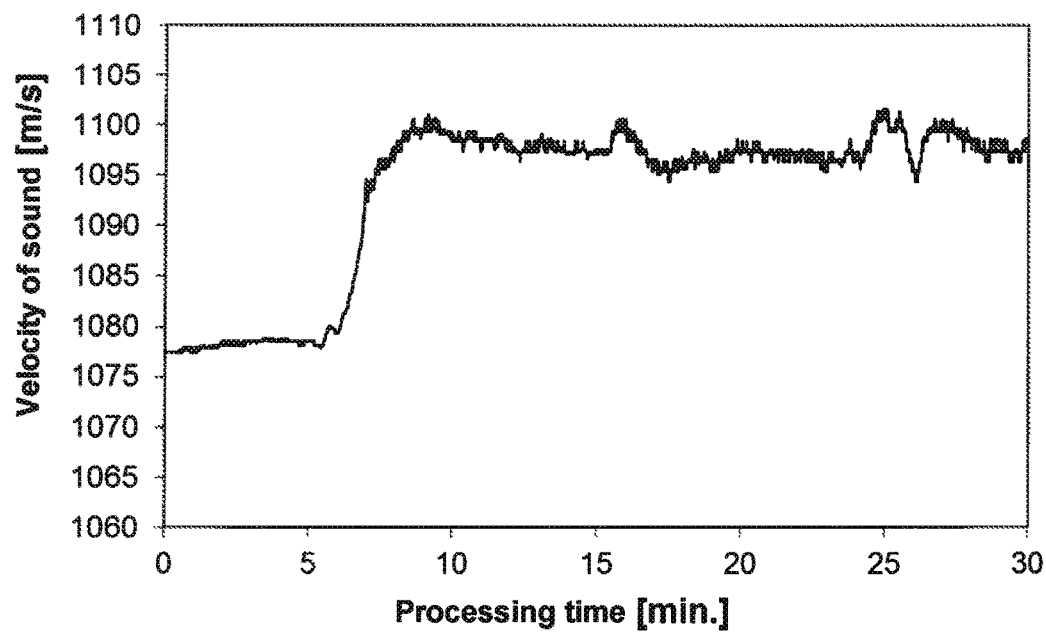
FIG. 6 provides an example of comparative test data showing the velocity of sound in the rubber mixtures of FIG. 5 as a function of processing time.

Four parent rubber mixtures using in each case about 1.2 kg were produced in a 1.5 l kneader from Gumix S.A. The rotation rate was 30 rpm, the fill level of the kneader was 70% and the mixing temperature was about 100° C. Parent mixture 1 comprised 100 phr of SMR10 natural rubber and 1 phr of stearic acid. Said parent mixture 1 was mixed in the kneader for about 5 min. and a milled sheet was molded from said mixture within 1 minute on a two-roll mill from Rubicon Gummitechnik und Maschinentechnik GmbH. Parent mixture 2 comprised, in addition, 50 phr of N110 carbon black, and was mixed by a method corresponding to that for parent mixture 1. Parent mixture 3 corresponded to parent mixture 2 except that it was mixed in the kneader for only 2 min. Parent mixture 4 likewise corresponds to parent mixture 2, except the mixture was mixed for only 1 minute. The different mixing procedures gave different levels of dispersion and of deagglomeration of the filler. The N110 carbon black had been supplied in the form of pellets (agglomerated filler entities), the diameter of which was in the range≤2 mm. The four different mixtures were introduced in succession into the extruder as in example 1, and the relative attenuation coefficient $\alpha_{rel.}(t)$, and the velocity of sound v were determined. When intensity I(t) was calculated here, the standardization used the average intensity $I_{average}$ for parent mixture 1 without carbon black at from t=0 min. to t=7 min. FIG. 6 shows the measurements for all 4 of the parent mixtures, where said mixtures were introduced in succession into the extruder and tested in succession, see table below.

| Parent mixture | Processing time [min] |
|---|---|
| 1 | 0-7 |
| 2 | 8-15 |
| 3 | 16-24 |
| 4 | 24-30 |

Figure 5:
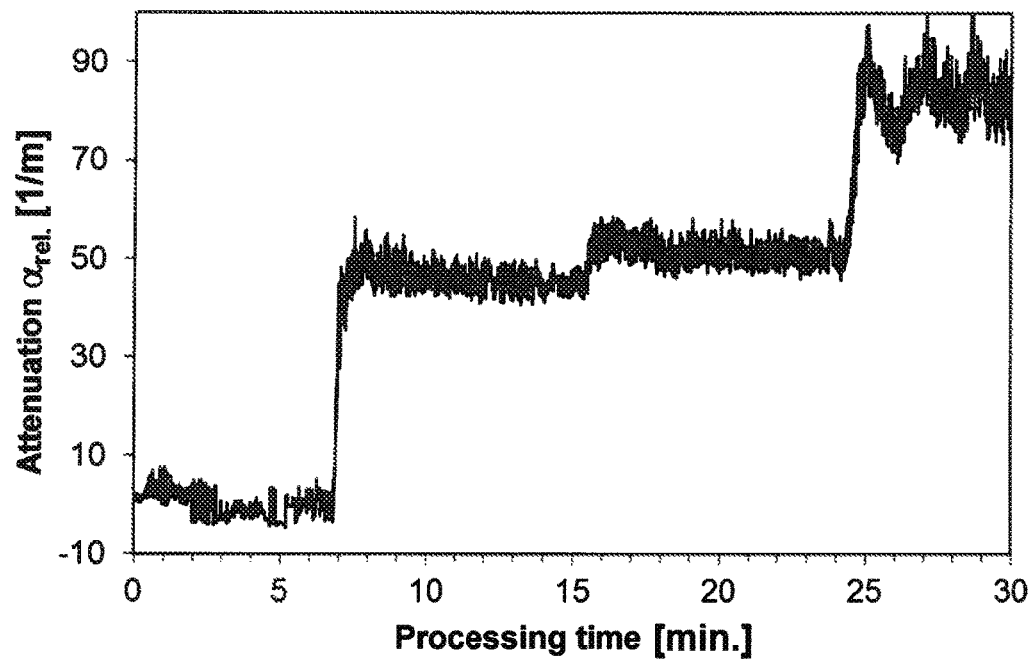
FIG. 5 provides an example of comparative test data showing the relative attenuation coefficient for various uncrosslinked rubber mixtures.

From FIG. 5 it can be seen that ultrasound attenuation is markedly greater for parent mixture 2 than for parent mixture 1 without carbon black. Attenuation for parent mixture 3 with a mixing time of only 2 minutes and with higher content of particulate contaminants is higher than for parent mixture 2. Furthermore, standard deviation from the average value of the relative attenuation coefficient is markedly higher for parent mixture 3 than for parent mixture 2. Parent mixture 4, with only 1 minute of mixing time, has very little deagglomeration of the filler, i.e. has a large number of coarse-particle contaminants. Here, the relative attenuation coefficient and the standard deviation are again markedly higher than for parent mixtures 2 and 3. Table 2 and FIG. 5 provide impressive evidence that different mixtures (parent mixtures 1 to 4) can be distinguished unambiguously from one another by the process of the invention. Said process can therefore provide detection of the different degree of dispersion and level of deagglomeration.

FIG. 6 shows the velocity of sound v(t) as a function of processing time t. The velocity is calculated by dividing the path length s by the time $t_{US}$ required by the needle pulse to travel a distance s between transmitter and receiver.

$$v = s/t_{US}$$

In contrast, the velocity of sound in the parent mixtures with carbon black differs only slightly as a function of the mixing time in the kneader (FIG. 6), since the concentrations of carbon black in the detection volume are identical in parent mixtures 2-4. However, the velocity of sound is markedly lower for parent mixture 1 without carbon black. It is thus possible to exclude quality-determining criteria other than the different degree of dispersion measured by means of the time-dependent relative-attenuation-coefficient function.

The velocity v(t) remains unaltered, unlike the relative attenuation coefficient. This shows that the latter is attributable exclusively to the coarse-particle contaminants, and not to the parent mixture.

The result shows that coarse contaminants can be detected in a rubber mixture by the process of the invention. The method is rapid. A batch of about 1 kg of mixture was tested within a few minutes without any great manual effort. The method is moreover representative, since the 7 mm diameter of the oscillator of the ultrasound sensor covers almost half of the 15 mm width of the flow channel.

Furthermore, the entire amount tested from the various mixtures within 30 minutes was more than 4 kg.

Comparative Experiments

The methods known from the prior art provide 5 measurements of Mooney viscosity for a mixture. The time required here is about 30 min inclusive of sample preparation. For four mixtures, the time required is then about 2 hours. The cause can moreover not be directly identified as coarse-particle contaminants. That requires preparation of an optical micrograph. Optical micrographs likewise require about 2 minutes per individual sample. A large number of individual samples must moreover be taken here. Furthermore, it is difficult to prepare optical micrographs of uncrosslinked rubber mixtures. Both of the processes known from the prior art moreover test markedly less material than the ultrasound process. This process tests about half of the material of the mixture. The process of the invention is therefore more representative and less time-consuming than the conventional methods.

What is claimed is:

1. A process for inline detection of particulate contaminants having a diameter >10 μm in a flow of uncrosslinked rubber mixture during processing of the rubber mixture in a rubber processing system, the process comprising:
   flowing uncrosslinked rubber mixture comprising rubber, filler, and cross-linking agent through a flow channel of the rubber processing system during processing of the rubber mixture, wherein the rubber mixture has a temperature >80° C.;
   projecting an ultrasound signal having a frequency of 0.5 MHz to 20 MHz through the uncrosslinked rubber mixture over a distance ≥10 mm at the temperature >80 ° C. during flow of the rubber mixture through the flow channel of the system;
   measuring at least one of:
      intensity of the ultrasound signal through the rubber mixture; and
      velocity of the ultrasound signal through the rubber mixture during flow of the rubber mixture through the flow channel of the processing system, wherein the ultrasound signal through the rubber mixture without particulate contaminants has first intensity and a first velocity, and the ultrasound signal through the rubber mixture with particulate contaminants has at least a second intensity and at least a second velocity;
   determining variations in the intensity and/or velocity of the ultrasound signal caused by a presence of particulate contaminants, wherein a pre-determined difference the first intensity and the second intensity and/or the first velocity and the second velocity provides an indication of the presence of particulate contaminants having a diameter >10 μm; and
   signaling detection of the particulate contaminants having a diameter >10 μm when the pre-determined difference in intensity and/or velocity provides an indication of the presence of particulate contaminants having a diameter >10 μm.

2. The process according to claim 1, wherein measuring of a decrease in intensity indicates the presence of particulate contaminants.

3. The process according to claim 2, wherein the velocity is indicative of particle size of the particulate contaminants, with larger particles having less slowing of the velocity, and wherein comparing of the measured velocities provides an indication of the presence of particulate contaminants having a diameter >10 µm as compared to particulates of smaller diameter.

4. The process according to claim 3, wherein the flow channel comprises a detection band comprising at least one pair of ultrasound sensors spaced apart from one another by the ≥10 mm distance, wherein one sensor of the pair comprises an ultrasonic transmitter for transmitting a signal through the rubber mixture, and the other sensor of the pair comprises an ultrasonic receiver for detecting the ultrasonic signal upon passage through the rubber mixture, and the method further comprises passing the uncrosslinked rubber mixture through detection band.

5. The process according to claim 4, wherein the detection band is composed of at least 2 of the sensor pairs arranged adjacent one another.

6. The process according to claim 5, wherein:
the uncrosslinked rubber mixture is flowing past the sensors in a stream having a width and the detection band is composed of an array of the sensor pairs arranged adjacent one another across the entire width of the uncrosslinked rubber mixture; and
the method further comprises ultrasonically scanning an entire cross-section of the uncrosslinked rubber mixture as the rubber mixture passes through the detection band.

7. The process according to claim 6, wherein the process further comprises, upon detection of particulate contaminants having a diameter >10 µm, removing the portion of the flow of the rubber mixture containing the contaminants from the flow channel.

8. The process according to claim 7, wherein:
the system comprises an extruder and the projecting and measuring occur along a portion of the extruder;
the portion of the flow containing the contaminants is removed upon exiting of the extruder;
the frequency is 2 MHz to 10 MHz;
the distance is ≥20 mm; and
the particulate contaminants have a diameter >100 µm with a melting temperature greater than the temperature of the uncrosslinked rubber mixture when the ultrasonic measurement is being made.

9. The process according to claim 8, wherein:
the temperature is greater than 100° C.;
the frequency is 4 MHz to 7 MHz;
the distance is ≥30 mm; and
the particulate contaminants have a diameter >500 µm.

10. An apparatus for processing an uncrosslinked rubber mixture and detecting particulate contaminants having a diameter greater than 10 µm in the uncrosslinked rubber mixture during processing thereof, the apparatus comprising:
an extruder;
at least one detection band disposed along the extruder, wherein the detection band comprises at least 2 ultrasound sensor pairs arranged alongside one another wherein sensors of each sensor pair are spaced apart from one another by ≥10 mm, and one sensor of each pair comprises an ultrasonic transmitter for sending an ultrasonic signal of 0.5 MHz to 20 MHz through the rubber mixture, and the other sensor of each pair comprises an ultrasonic receiver for detecting at least one of:
intensity of the ultrasonic signal upon passage through the rubber mixture; and
velocity of the ultrasonic signal upon passage through the rubber mixture; and
at least one processing unit for conducting and evaluating the process as claimed in any of claim 1, 2, 3 or 6.

11. A process for the detection of particulate contaminants having a diameter >10 µm in a flow of uncrosslinked rubber mixture during processing of the rubber mixture in a processing system, the process comprising:
projecting an ultrasound signal having a frequency of 0.5 MHz to 20 MHz through the uncrosslinked rubber mixture over a path length (s) during flow of the rubber mixture through the processing system;
measuring intensity of the ultrasound signal through the rubber mixture during flow of the rubber mixture through the processing system, wherein the ultrasound signal through the rubber mixture without particulate contaminants has at least a first intensity ($I_{average}$), and the ultrasound signal through the rubber mixture with particulate contaminants at a time (t) has at least a second intensity (I);
calculating a relative attenuation coefficient $\alpha_{rel.}$ at a processing time (t), wherein:

$$\alpha_{rel.}(t) = -\ln(I(t)/I_{average})/s$$

wherein a predetermined increase in $\alpha_{rel.}$ is indicative of presence of contaminants having a diameter >10 µm; and
determining the presence of contaminants when $\alpha_{rel.}$ is greater than a predetermined value.

* * * * *